(12) United States Patent
Gao et al.

(10) Patent No.: US 8,445,026 B2
(45) Date of Patent: May 21, 2013

(54) SELENIUM NANOPARTICLES WITH IMPROVED BIOLOGICAL EFFECTS

(76) Inventors: Xueyun Gao, Beijing (CN); Yi Sun, Malden, MA (US)

(*) Notice: Subject to any disclaimer, the term of this patent is extended or adjusted under 35 U.S.C. 154(b) by 846 days.

(21) Appl. No.: 12/275,647

(22) Filed: Nov. 21, 2008

(65) Prior Publication Data

US 2012/0207846 A1 Aug. 16, 2012

Related U.S. Application Data

(60) Provisional application No. 61/004,793, filed on Dec. 1, 2007.

(51) Int. Cl.
*A61K 31/095* (2006.01)
*A61K 9/14* (2006.01)

(52) U.S. Cl.
USPC ............. 424/499; 514/706; 514/1.1; 514/5.5; 514/21.92

(58) Field of Classification Search
USPC .................. 424/499; 514/706, 1.1, 5.5, 21.92
See application file for complete search history.

(56) References Cited

PUBLICATIONS

Li et al. Rapid Room-temperature synthesis of amorphous selenium/protein composites using Capsicum annuum L extract, Nanotechnology, 18, Published Sep. 11, 2007, pp. 1-9.*
Zhang et al., Biological effects of a nano red elemental selenium, BioFactors 15, Published in 2001, pp. 27-38.*
Zhang et al., Synthesis of selenium nanoparticles in the presence of polysaccharides, Materials Letters, 58, 2004, 2590-2594.*
Huang et al., Free radical scavenging efficiency of nano-se in vitro, Free Radical Biology and Medicine, vol. 35, No. 7, 2003, 805-813.*
Abdelouas et al., Using cytochrome c3 to make selenium nanowires, Chem. Mater. 2000, 12, 1510-1512.*
Zhang et al. (Materials Letters, 58, Published 2004, pp. 2590-2594).*
Allan (The Practice of Commercial Organic Analysis, vol. II, p. 381, Published 1882).*
Butler et al. (Journal of the American Chemical Society, vol. 51, Published 1929, pp. 1519-1525).*
Dictionary of Food Science and Technology, Second Edition, Published 2009, p. 28.*
Stroyuk et al. (Colloids and Surfaces A: Physicochemical Engineering Aspects, 320, Available on line Mar. 10, 2008, pp. 169-174).*

* cited by examiner

*Primary Examiner* — Richard Schnizer
*Assistant Examiner* — Alma Pipic
(74) *Attorney, Agent, or Firm* — Jie Tan

(57) ABSTRACT

Novel methods for biological effective, stable amorphous and monoclinic selenium nanoparticles are disclosed. They are prepared by reacting selenium source with a reducing agent or an oxidative agent in an aqueous media at a temperature between 0-100° C. in the presence of selenium binding polymer molecules such as poly/oligopeptide acids or peptone or nucleic acids or poly/oligosaccharide or their mixtures.

7 Claims, 6 Drawing Sheets

SELENIUM NANOPARTICLES WITH IMPROVED BIOLOGICAL EFFECTS

CROSS-REFERENCE

Priority is claimed from the U.S. Provisional Application 61/004,793, filed on Dec. 1, 2007, which is hereby incorporated by reference.

BACKGROUND

The present application relates to biologically effective forms of selenium, and more particularly to monoclinic and amorphous selenium nanoparticles having a size of 1-300 nm; also disclosed are the methods and processes of making such nanoparticles.

Note that the points discussed below may reflect the hindsight gained from the disclosed inventions, and are not necessarily admitted to be prior art.

Selenium is an essential micronutrient for man and animals. The main form of selenium in mammalian is its presence in selenoproteins as selenocysteine (Sec) encoded by the TGA codon in DNA. Sec with its stronger nucleophilicity plays an essential role in some enzyme activities as a key catalytic group. Other biological effects include its anti-oxidative effects.

Selenite and selenate from food and water are used by mammalian cells as selenium sources, and selenite is reduced to selenide by the glutathione-glutaredoxin and the thioredoxin systems, which is used as However, the toxicity of inorganic selenium compounds, e.g. selenite and selenate, is also well known. It has been a challenge for researchers to develop a food supplement using inorganic selenium compounds.

Reducing selenate and selenite to elemental selenium (Se(0)) by certain fungi and bacteria has been shown to result in detoxification. See Gharieb, M. M., et al. "Reduction of selenium oxyanions by unicellular, polymorphic and filamentous fungi: cellular location of reduced selenium and implications for tolerance," J. of Industrial Microbiology, 14, 300-31, 1995; and Oremland, R. S., et al., "Structural spectral features of selenium nanospheres produced by Se-respiring bacteria," Applied and Environmental Microbiology, 70, p 52-60, 2004 (herein after referred to as Oremland).

The detoxicated elemental selenium Se(0) exists both intracellularly and extraculluallarly, some as monoclinic crystals in nanoparticle form (nano-Se) with size around 300 nm. See Oremland. Besides monoclinic selenium, other forms of elemental selenium particles also exist in nature. However, grey and black forms of micrometer size (vitreous, insoluble Se(0) particles) are biologically inert, while the red colloidal selenium nano-particles are biologically effective. See Zhang, J., et al., "Biological effects of a nano red elemental selenium," BioFactors, 15, page 27-38, 2001 (herein after referred to as Zhang). The entirety of which is hereby incorporated by reference.

It has been shown that the size of elemental selenium nanoparticles plays an important role in their biological activity. For example, as expected, 5-200 nm Nano-Se can directly scavenge free radicals both in vitro and in vivo in a size-dependent fashion. See Peng, D, et al., "(Nano-Se) at supra-nutritional levels on selenium accumulation and glutathione S-transferase activity," J. Inorganic Biochem., v. 101, p 1457-1463, October 2007, the entirety of which is hereby incorporated by reference. Because of its bioavailability and higher bioeffects, nano-Se has drawn increasingly greater attention in efforts to develop selenium nutritional supplements and in medical uses.

Although methods to prepare the colloid of amorphous selenium are reported, the produced selenium colloids are unstable, and they easily aggregate together to form micro-sized particles and change into a trigonal crystal form which is not biologically effective.

There is great need to produce stable and well-dispersed selenium nano-particles in monoclinical or colloidal form of biologically effective size for improved biological effects.

BRIEF DESCRIPTION OF THE DRAWINGS

The disclosed inventions will be described with reference to the accompanying drawings, which show important sample embodiments of the invention and which are incorporated in the specification hereof by reference, wherein.

DETAILED DESCRIPTION OF SAMPLE EMBODIMENTS

Figure 1:
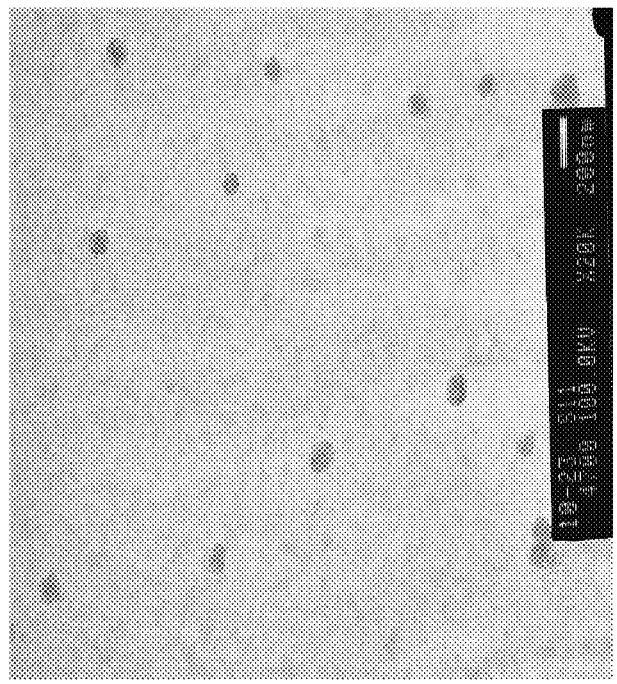
FIG. 1 shows a transmission electron micrograph of a field of selenium particles of example 1 that have particle sizes between 22 nanometers to 70 nanometers.
Figure 2:
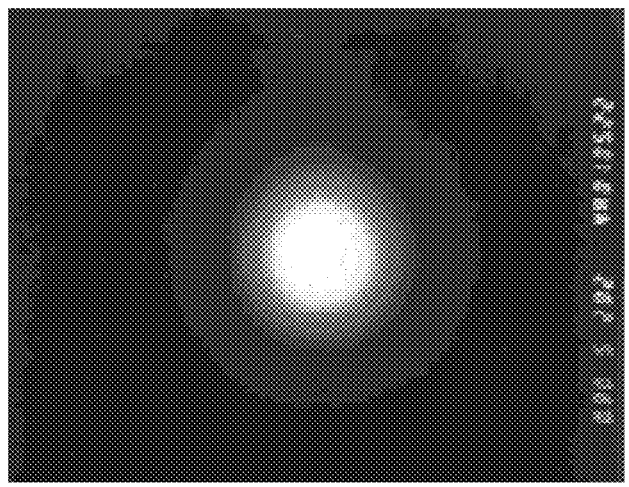
FIG. 2 shows an electron diffraction pattern of selenium nanoparticles of example 2 that have an amorphous form.

The numerous innovative teachings of the present application will be described with particular reference to presently preferred embodiments (by way of example, and not of limitation). The present application describes several inventions, and none of the statements below should be taken as limiting the claims generally.

For simplicity and clarity of illustration, the drawing figures illustrate the general manner of construction, and description and details of well-known features and techniques may be omitted to avoid unnecessarily obscuring the invention. Additionally, elements in the drawing figures are not necessarily drawn to scale, some areas or elements may be expanded to help improve understanding of embodiments of the invention.

The terms "first," "second," "third," "fourth," and the like in the description and the claims, if any, may be used for distinguishing between similar elements and not necessarily for describing a particular sequential or chronological order. It is to be understood that the terms so used are interchangeable. Furthermore, the terms "comprise," "include," "have," and any variations thereof, are intended to cover non-exclusive inclusions, such that a process, method, article, apparatus, or composition that comprises a list of elements is not necessarily limited to those elements, but may include other elements not expressly listed or inherent to such process, method, article, apparatus, or composition. The terms nano-particles, nanospheres, nano-Se are used interchangeably in this application, they all represent the elemental selenium particles formed in the reactions described herein.

The applicant found that nanometer-scale particles of elemental selenium can be produced by direct reaction of a selenium source with a reducer or an oxidant source in the presence of selenium binding macromolecules. Moreover, the applicant found that the selenium binding macromolecules can mediate the size of the obtained selenium particles by adsorbing to the surface of the selenium particle through affinity between selenium and nitrogen/oxygen of the macromolecles, which insures the selenium particles be well dispersed, not to aggregate, in aqueous solution and be kept in amorphous and monoclinic status.

The present application discloses novel approaches to make biologically effective elemental selenium nanoparticles.

In one embodiment, the sizes of the selenium nanoparticles range from 1 nm to 300 nm.

In another embodiment, the selenium in the nanoparticles comprises amorphous (colloidal) selenium.

In another embodiment, the selenium nanoparticles comprise monoclinic selenium, or the mixture of both amorphous and monoclinic selenium.

In another embodiment, the surfaces of selenium nanoparticles bind various selenium binding biological molecules, such as peptones, or poly/oligopeptides, or nucleic acids, or poly/oligosaccharides, or a mixture thereof.

The selenium binding molecules are selected from a group of peptones from soybean, peptones from animal tissue, peptones from animal protein, peptones from casein, peptones from gelatin, peptones from lactalbumin, peptones from meat, mycological peptones, poly-Lysine hydrochloride, poly-arginine, poly(Arg, Pro, Thr)hydrochloride, poly(Arg, Trp)hydrochloride, poly-asparagine, poly-aspartic acid sodium salt, poly-aspartic acid sodium salt, poly-glutamate, deoxyribonucleic acid from calf thymus, deoxyribonucleic acid sodium salt from herring, deoxyribonucleic acid sodium salt from salmon, deoxyribonucleic acid sodium salt from calf thymus, deoxyribonucleic acid sodium salt from human placenta, ribonucleic acid from baker's yeast, ribonucleic acid from torula yeast, ribonucleic acid diethylaminoethanol salt from torula yeast, peptidoglycan, polysaccharide, and oligosaccharide and the combinations thereof.

The disclosed innovations, in various embodiments, provide one or more of at least the following advantages. However, not all of these advantages result from every one of the innovations disclosed, and this list of advantages does not limit the various claimed inventions.

Better bioavailability, and less toxicity;
More biologically effective;
Can be used as a more effective nutritional supplement;
More cost effective to prepare.

Generally, a selenium source compound, for example, sodium selenite, is combined in approximately four times molar ratio with a reducer compound, for example, citric acid. These materials are first dissolved in an aqueous selenium binding macromolecule containing reaction medium. The selenium binding macromolecules in the reaction medium have the effect of halting and stopping selenium particle's further aggregating when the particles reach a size of 1-300 nanometer across. Selenium binding macromolecules include polymeric molecules that are either a polymer or an oligomer nucleotides, glycans, peptides or soluble protein and nucleic acid molecules. These selenium binding macromolecule materials may bind to the surface of the formed selenium particle, presenting a repulsive force between selenium particles and thus preventing further aggregation of the particles. Absence of selenium binding macromolecule in the reaction medium the reaction will produce amorphous or monoclinic elemental selenium particles that will quickly aggregate and become trigonal selenium micrometer sized particles that are insoluble and biologically inert.

In this disclosure the red-ox agents can be either a reducing agent or an oxidative agent that can reduce or oxidize a selenium source into elemental selenium.

Example reaction with reducing agent, such as L-Glutathione,

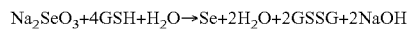

With oxidative agent, such as $H_2O_2$

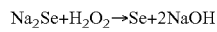

The produced Se(0) will aggregate to form Se(0) nanoparticles, which are composed hundred of thousand Se atom and coated by peptone or other chemicals.

In the preferred embodiment, the reaction medium is aqueous and contains at least one type of selenium binding macromolecule. The selenium binding macromolecule contains nitrogen of amine or nucleic acid base which complex with selenium atom of the produced selenium particle and bind to their surface, thereby preventing further particle growth.

In the preferred embodiment, the amount of the selenium binding macromolecule should be compatible with the reactive components and constitute at least about 0.01% (by mass ratio) and preferably at least about 0.1%, and may be up to 80%, of the aqueous reaction medium. Mixtures of two or more selenium binding macromolecules may be used if desired.

In the preferred embodiment, the selenium binding macromolecules include peptones, poly/oligopeptide, nucleic acid, poly/oligosaccharide. The examples can be peptones from soybean, peptones from animal tissue, peptones from animal protein, peptones from casein, peptones from gelatin, peptones from lactalbumin, peptones from meat, mycological peptones, poly-Lysine hydrochloride, poly-arginine, poly (Arg, Pro, Thr)hydrochloride, poly(Arg, Trp)hydrochloride, poly-asparagine, poly-aspartic acid sodium salt, poly-aspartic acid sodium salt, poly-glutamate, deoxyribonucleic acid from calf thymus, deoxyribonucleic acid sodium salt from herring, deoxyribonucleic acid sodium salt from salmon, and deoxyribonucleic acid sodium salt from calf thymus, deoxyribonucleic acid sodium salt from calf thymus, In the preferred embodiment, the selenium source, such as a selenium salt, or selenium acid is reacted directly with a reducer agent, such as chemicals with thiols or hydroxyls, or an oxidant, such as $O_2$ or $O_3$ or $H_2O_2$ or radical oxygen species. Other representative selenium sources include H2Se, $H_2SeO_3$, $H_2SeO_4$, $Na_2SeO_3$, $Na_2SeO_4$, $Na_2SSeO_3$, $H_2SSeO_3$, or the like as may be obvious to a person skilled in the art.

Other representative reducer include cysteine, GSH, ascorbic acid, thioalcohol, citric acid, L-glutathione, L-ascobic acid, citrate, thioacetamide, 2-thio-6-azauridine, thiobacillus broth, 2-thiobarbituric acid, 2-thiocytosine, 1-thioglycerol, thioglycolate broth, thioglycolic acid, 6-thioguanine, thiolactic acid, thiomalic acid, 2-thiopurine, thiourea, 4-thiouridine or the like as may be obvious to a person skilled in the art. Mixtures of two or more selenium salts with two or more reducer agents may be used.

In the preferred embodiment, one or more of each of these two groups of materials are mixed in the aqueous reaction medium that contains selenium binding molecules at a temperature between 0-100° C. for a period of less than 24 hours.

The preferred reaction temperature varies as to different reactants and different selenium binding molecules in the reaction medium.

For example, the reaction of sodium selenite with L-cysteine in an about 1:4 molar ratio in an aqueous reaction containing peptone from soybean can be conducted at a temperature around 40° C. The reaction of sodium selenide with H2O2 in about 1:1 molar ratio in a peptidoglycan containing aqueous solution is preferred to be conducted at a temperature around 80° C. The reaction of sodium selenite with sodium citrate in about 1:6 molar ratio in a poly-Lysine hydrochloride containing aqueous solution is preferred to be conducted at a temperature around 80° C. The reaction of sodium selenite with sodium citrate in about 1:6 molar ratio in an arabinan containing aqueous solution is preferred to be conducted at a temperature around 80° C. The reaction of selenite acid with L-ascorbic acid in an about 1:4 molar ratio in a ribonucleic acid from torula yeast containing aqueous reaction phase is preferred to be conducted at a temperature around 70° C.

The final product is the selenium binding molecule containing selenium nanoparticles of a proper size of 1-300 nm across.

The reaction can be carried out in the aqueous reaction medium at a 1:4 molar ratio of selenium salt/acid to thiols/hydroxyls. This ratio can be varied such as from 1:32 to 8:1 without much effect on the quality of the final product. The concentration of reactants in the reaction medium can range from about 5 μmolar (basis selenium salt) to about 0.5 molar. Good results are obtained from 50 μmolar to 0.5 molar, although higher and lower concentrations can also be used. The reaction zone can be agitated by a stirrer, if desired.

The product of the reaction is a nanoparticle powder which can be isolated by simply removing the water reaction medium. This is carried out by evaporation, filtration and the like which would be obvious to a person skilled in the art.

EXAMPLES

This disclosure will be further described by the following Examples. These Examples are not to be construed as limiting the scope of this invention, which is defined by the appended claims.

Example 1

Sodium selenite (99.99%), L-cysteine (99.99%), peptone from soybean (80%) were purchased from Sigma, and stored in a dry box. Water was distilled prior to use. 50 g peptone from soybean was added to 1000 ml of 100 mM sodium selenite solution. The dissolved solution was continually added with L-cysteine to reach a final concentration of 400 mM. The resulting mixture was kept or stirred at 25° C. for 10 hours. Then sodium ions and oxidized-L-cysteine was removed by dialysis, a solution consisted of amorphous selenium particles and peptone was obtained. The resulted amorphous selenium particles were studied by TEM. As shown in FIG. 1, the nano-Se particles were deposited from the solution onto an amorphous carbon overlayer on a Cu grid and were imaged on a JEOL 2010 microscope operating at an accelerating voltage of 200 kV. In FIG. 1, the resulted nano-Se particles ranged from 22-70 nanometers, with an average size of 35 nanometer.

Example 2

In place of the L-cystiene of Example 1, ascorbic acid was used as the reducing agent. The preparation of Example 1 was repeated. Similar amorphous selenium nanoparticles as to Example 1 were obtained (data not shown).

Example 3

Figure 3:
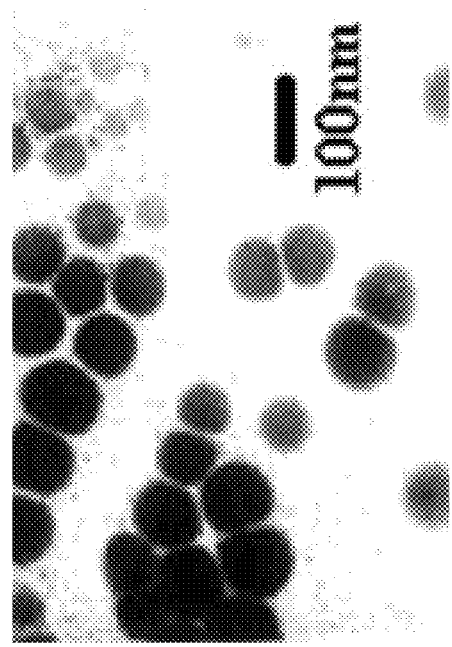
FIG. 3 shows a transmission electron micrograph of selenium particles of example 3 having sizes between 30 nanometers to 100 nanometers.

The preparation of Example 1 was repeated using sodium selenate in place of sodium selenite and the reaction temperature was at 50° C. As shown in FIG. 3, the product was a mixture of amorphous and monoclinic selenium nanoparticles ranging 30-100 nanometers.

Example 4

Figure 4:
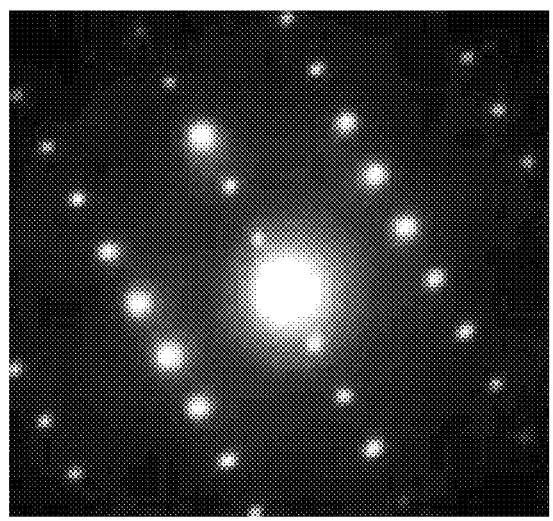
FIG. 4 shows an electron diffraction pattern of selenium nanoparticles of example 4 that show monoclinic crystal structure.

The same reaction as Example 1, except arabinan hydrochloride, a polysaccharide, was used as the selenium binding molecule in the reaction medium, the reaction was kept at 70° C. for 8 hours. As shown in FIG. 4, electron diffraction patterns showed that the product was elemental selenium nanoparticles in monoclinic crystal structure.

Example 5

Figure 5A:
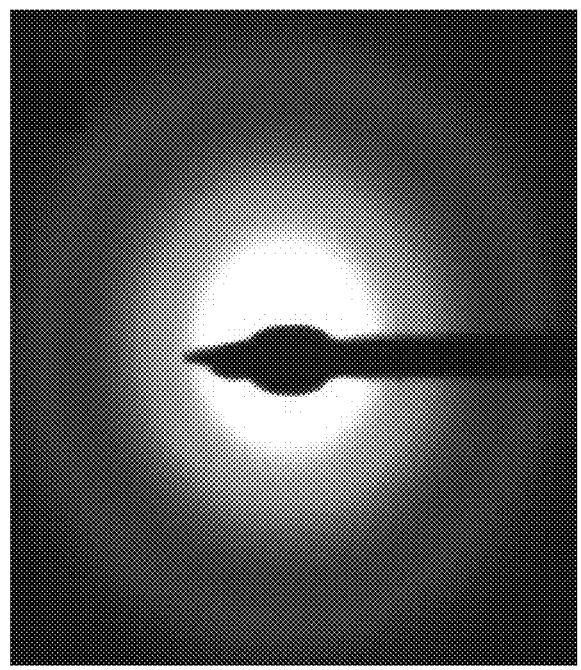
FIG. 5a shows an electron diffraction pattern of selenium nanoparticles of example 5 that show amorphous and monoclinic complex structure.
Figure 5B:
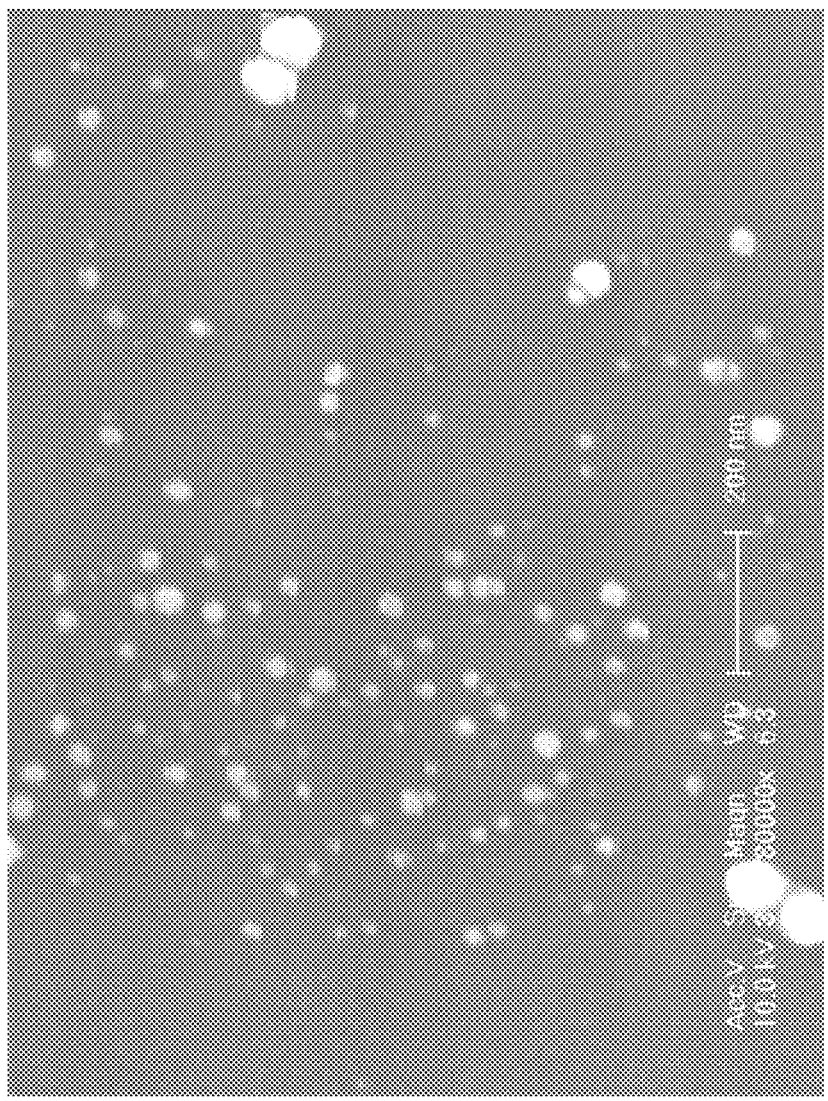
FIG. 5b shows a scanning electron micrograph of selenium particles of example 5 having sizes between 10 nanometers to 200 nanometers.

Example 1 was repeated using a $Na_2SSeO_3$ in place of sodium selenite, and 1 mM H2O2 oxidant in place of reducer agent L-cysteine. In addition, deoxyribonucleic acid (single stranded from calf thymus, MW~50 kb) was used in the reaction medium, in place of peptone. As shown in FIG. 5*a* and FIG. 5*b*, the produced selenium nanoparticles were in amorphous and monoclinic complex structure.

According to various embodiments, there is provided: A method for forming elemental selenium nano-particles, comprising the steps of: reacting a reaction-medium soluble selenium source with a reaction-medium soluble red-ox agent in a reaction medium at a temperature between 0-100° C. for a period of time, wherein said reaction medium contains an elemental selenium binding polymeric molecule that is selected from the group consisting of peptones, polypeptides, and oligopeptides and the combination thereof, and recovering nano-particles of sizes between 1-300 nm.

According to various embodiments, there is provided: An elemental selenium nanoparticle, comprising: elemental selenium atoms aggregated as a nano-particle in size between 1-300 nm; and a selenium binding polymeric molecule wherein said macromolecule is selected from a group comprising peptones, peptides, polypeptides, nucleic acids, polysaccharides, oligosacchrides and the hybrid molecules thereof, and at least partly complexed with said selenium atoms of said nano-particle.

According to various embodiments, there is provided: A method for forming elemental selenium nano-particles, comprising the steps of: reacting a reaction-medium soluble selenium source with a reaction-medium soluble red-ox agent in a reaction medium at a temperature between 0-100° C. for a period of time, wherein said reaction medium contains an elemental selenium binding polymeric molecule that is not bovine serum albumin (BSA); and recovering nano-particles of sizes between 1-300 nm.

According to various embodiments, there is provided: A method for forming elemental selenium nano-particles, comprising the steps of: reacting a soluble selenium source with a soluble oxidation-state-changing agent in a reaction medium at a temperature between 0-100° C. for a period of time, wherein said reaction medium contains an elemental selenium binding polymeric molecule that is substantially non-immunogenic; and recovering nano-particles of sizes between 1-300 nm.

According to various embodiments, there is provided: Novel methods for biological effective, stable amorphous and monoclinic selenium nanoparticles are disclosed. They are prepared by reacting selenium source with a reducing agent or an oxidative agent in an aqueous media at a temperature between 0-100° C. in the presence of selenium binding polymer molecules such as poly/oligopeptide acids or peptone or nucleic acids or poly/oligosaccharide or their mixtures.

Modifications and Variations

As will be recognized by those skilled in the art, the innovative concepts described in the present application can be modified and varied over a tremendous range of applications, and accordingly the scope of patented subject matter is not limited by any of the specific exemplary teachings given. It is intended to embrace all such alternatives, modifications and variations that fall within the spirit and broad scope of the appended claims.

In this disclosure the red-ox agents can be either a reducing agent or an oxidative agent that can reduce or oxidize a selenium source into elemental selenium.

Polypeptides, nucleic acid, and polysaccharide macromolecules used in the claims are crude digestion extracts from various biological sources, including plants, animals, bacteria and fungi, and the standard forms are readily available from a commercial source, such as Sigma, Fisher or other biotechnology companies. Other crude extracts, generally known to a person skilled in the art, for example, other commercially available crude protein or tissue digestion extracts that have been used for bacteria, fungus culture, etc. can also be used for the innovation disclosed herein. A mixture of various lengths and molecule types have been used. The selenium binding polymeric molecules should also include any form of hybrid macromolecules and molecules with modifications, for example, nucleo-proteins, or digestion products of nucleo-proteins, peptidal-polysacchrides, polysacachride nucleic acid, and their modified molecules, such as methylated nucleic acid, and lipoproteins, etc.

Additional general background, which helps to show variations and implementations, may be found in the following publications, all of which are hereby incorporated by reference:

1. Gao, Xueyun et al., (2000) Weisheng Yanjiu, 29(1), 57-58;
2. Gao, Xueyun et al., (2000) Zhongguo Gonggong Weisheng, 16(5), 421-422;
3. Gao, Xueyun et al., (2000) Zhongguo Gonggong Weisheng, 16(2), 109-110;
4. Gao, Xueyun et al., (2002) Advanced Materials, 14(4), 290-293;
5. Jiri Touzin et al., (2002) Collection of Czechoslovak Chemical Communications, 67(5), 577-586;
6. Hiroto Komatsu et al., (1999) Chem. Commun., 205-206;
7. Zhang, Jin-Song et al., (2001), BioFactors 15, 27-38;
8. Zhang, Jinsong, et al, (2007), ToxSci Advance Access, p 1-30;
9. Tomei, F. A. et al., (1995) Journal of Industrial Microbiology, 14, 329;
10. Gharieb, M. M. et al., (1995) Journal of Industrial Microbiology, 14, 300;
11. Nuttall, K. L., (1987) Med. Hypotheses, 24, 217;
12. Ammerman, C. B. et al., (1975) Journal Dairy Science, 58, 1561;
13. (1987) WHO working group, Environmental Health Criteria, 58, 300-310;
14. B. Gates et al, (2002) Advanced Functional Materials, 12, 221
15. Oremland et al, (2004) Applied and Environmental Microbiology, 70, 52.
16. Peng, Dungeng; et al., (2007) Journal of Inorganic Biochemistry 101, p 1457-1464.

None of the description in the present application should be read as implying that any particular element, step, or function is an essential element which must be included in the claim scope: THE SCOPE OF PATENTED SUBJECT MATTER IS DEFINED ONLY BY THE ALLOWED CLAIMS. Moreover, none of these claims are intended to invoke paragraph six of 35 USC section 112 unless the exact words "means for" are followed by a participle.

The claims as filed are intended to be as comprehensive as possible, and NO subject matter is intentionally relinquished, dedicated, or abandoned.

What is claimed is:

1. A 1-300 nm sized biologically effective elemental selenium nanoparticle, comprising:
   a plurality of elemental selenium atoms; and
   at least one selenium binding molecule wherein said binding molecule is selected from the group consisting of peptone from soybean protein digestion, peptone from animal protein digestion, peptone from casein digestion, peptone from gelatin digestion, peptone from lactalbumin digestion, mycological peptone, poly-Lysine hydrochloride, poly-arginine, poly(Arg, Pro, Thr) hydrochloride, poly(Arg, Trp) hydrochloride, poly-asparagine, poly-aspartic salt, and polyglutamate salt wherein said binding molecule is at least partly complexed with said plurality of selenium atoms forming a nanosphere of 1-300 nm in size that is stable in solution and wherein said selenium atoms are aggregated either in amorphous or monoclinic form.

2. The selenium nanoparticle of claim 1, wherein the selenium atoms are generated from a selenium source solution selected from a group consisting of selenium salts, $H_2SeO_3$, $H_2SeO_4$, $Na_2SeO_3$, $Na_2Se$, $H_2Se$, $Na_2SeO_4$, $Na_2SSeO_3$, and $H_2SSeO_3$.

3. The selenium nanoparticle of claim 2, wherein the selenium atoms are generated by mixing said selenium source solution with a redox agent in a solution containing said selenium binding molecule at a concentration of at least 0.01% by mass ratio relative to the reaction medium.

4. The selenium nanoparticle of claim 2, wherein said selenium atoms are generated by mixing said selenium source solution with a reducing agent selected from the group consisting of L-glutathione, L-cysteine, L-ascobic acid, citric acid, citrate, thioacetamide, 2-thio-6-azauridine, thiobacillus broth, 2-thiobarbituric acid, 2-thiocytosine, 1-thioglycerol, thioglycolate broth, thioglycolic acid, 6-thioguanine, thiolactic acid, thiomalic acid, 2-thiopurine, thiourea, and 4-thiouridine.

5. The selenium nanoparticle of claim 3 wherein said redox agent is $H_2O_2$.

6. The selenium nanoparticle of claim 3 wherein said selenium source and said redox agent is reacted at temperature higher than or equal to room temperature, at pH>6.

7. A 1-300 nm sized biologically effective elemental selenium nanoparticle comprising an elemental selenium binding molecule produced by a process comprising the steps of:
   reacting a reaction-medium-soluble selenium source with a reaction-medium-soluble redox agent in a reaction medium at a temperature between 0-100° C. for a sufficient period of time to reduce or oxidize the reaction-medium-soluble selenium source to obtain elemental selenium wherein said reaction medium contains an elemental selenium binding molecule selected from the group consisting of peptone from soybean protein digestion, peptone from animal protein digestion, peptone from casein digestion, peptone from gelatin digestion, peptone from lactalbumin digestion, mycological peptone, poly-Lysine hydrochloride, poly-arginine, poly(Arg, Pro, Thr) hydrochloride, poly(Arg, Trp) hydrochloride, poly-asparagine, poly-aspartic salt, and poly-glutamate salt, and wherein said selenium source is selected from a group consisting of selenium salts, $H_2SeO_3$, $H_2SeO_4$, $Na_2SeO_3$, $Na_2Se$, $H_2Se$, $Na_2SeO_4$, $Na_2SSeO_3$, and $H_2SSeO_3$, and wherein said redox agent is selected from the group consisting of L-glutathione, L-cysteine, L-ascobic acid, citric acid, citrate, thioacetamide, 2-thio-6-azauridine, thiobacillus broth, 2-thiobarbituric acid, 2-thiocytosine, 1-thioglycerol, thioglycolate broth, thioglycolic acid, 6-thioguanine, thiolactic acid, thiomalic acid, 2-thiopurine, thiourea, 4-thiouridine and $H_2O_2$.

\* \* \* \* \*